United States Patent
Brosz et al.

(10) Patent No.: US 8,435,568 B2
(45) Date of Patent: *May 7, 2013

(54) USE OF WF10 FOR TREATING ALLERGIC ASTHMA, ALLERGIC RHINITIS AND ATOPIC DERMATITIS

(75) Inventors: Mathias Brosz, Wanzleben-Blumenberg (DE); Friedrich-Wilhelm Kuhne, Wanzleben (DE); Klaus Blaszkiewitz, Heidelberg (DE); Thomas Isensee, Sulzetal (DE)

(73) Assignee: Nuvo Research AG, Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/560,032

(22) Filed: Jul. 27, 2012

(65) Prior Publication Data

US 2012/0294849 A1 Nov. 22, 2012

Related U.S. Application Data

(63) Continuation of application No. 12/602,589, filed as application No. PCT/EP2008/004312 on May 30, 2008, now Pat. No. 8,252, 343.

(60) Provisional application No. 60/941,438, filed on Jun. 1, 2007.

(51) Int. Cl.
*A01N 59/08* (2006.01)

(52) U.S. Cl.
USPC .......................................................... 424/661

(58) Field of Classification Search ........................ None
See application file for complete search history.

(56) References Cited

U.S. PATENT DOCUMENTS

| | | | |
|---|---|---|---|
| 4,507,285 A | 3/1985 | Kuehne | |
| 4,574,084 A | 3/1986 | Berger | |
| 4,725,437 A | 2/1988 | Kuehne | |
| 4,851,222 A | 7/1989 | Kuehne et al. | |
| 5,384,134 A | 1/1995 | Kross et al. | |
| 5,877,222 A | 3/1999 | McGrath | |
| 6,703,202 B2 | 3/2004 | McGrath et al. | |
| 8,252,343 B2 * | 8/2012 | Brosz et al. | 424/661 |
| 2005/0129784 A1 * | 6/2005 | Kuehne et al. | 424/661 |
| 2007/0145328 A1 | 6/2007 | Boulanger et al. | |
| 2009/0004295 A1 | 1/2009 | Kuehne et al. | |
| 2011/0076344 A1 | 3/2011 | Kuehne et al. | |

FOREIGN PATENT DOCUMENTS

| | | | |
|---|---|---|---|
| CA | 1174976 A * | 9/1984 | |
| EP | 0 200 156 B1 | 11/1986 | |
| EP | 0 200 157 B1 | 11/1986 | |
| EP | 0 561 145 B1 | 9/1993 | |
| JP | 60-500572 | 4/1985 | |
| JP | 9-511752 | 11/1997 | |
| WO | WO 96/28173 | 9/1996 | |

OTHER PUBLICATIONS

Office Action issued on Oct. 6, 2011 by the Examiner in U.S. Appl. No. 12/894,618 (US 2011/0076344).

(Continued)

*Primary Examiner* — Bethany Barham
(74) *Attorney, Agent, or Firm* — Foley & Lardner LLP

(57) ABSTRACT

The present invention provides a method of treating or inhibiting at least one of allergic asthma, allergic rhinitis and atopic dermatitis, or of reducing, inhibiting or treating allergy like symptoms. The methods use compositions comprising chlorite, chloride, chlorate and/or sulfate ions.

20 Claims, 1 Drawing Sheet

OTHER PUBLICATIONS

International Search Report issued on Sep. 12, 2008 in U.S. Appl. No. PCT/EP2008/004312.

Habermann et al., "Oxoferin and sodium chlorite—a comparison," Klin. Wochenschr., Jan. 4; 1989; 67(1); 20-5; (abstract).

Yu et al., "The reactivity of sera from patients with systemic lupus erythemotosus to seven different species of single and double stranded deoxyribonucleic acids," Clin. Exp, Rheumatol., vol. 14, No, 2, pp. 137-144 (abstract), 1996.

Levo et al., "Correlation between anti-DNA antibody titre and psychiatric manifestation in systemic lupus erythematosus," Postgrad Med. J. Dec. 1976; 52(614); 795-8 (abstract).

Schebesch et al.; "Alternatively Activated Macrophages Actively Inhibit Proliferation of Peripheral Blood Lymphocytes and CD4+ T Cells in Vitro"; Immunology; vol. 92; 1997; pp. 478-486.

Kodelja et al.; "Alternative Macrophage Activation-Assoc ated CC-Chemokine-1, A Novel Structural Homologue of Macrophage Inflammatory Protein 1-ct With a Th-2-Associated Expression Pattern"; The Journal of Immunology; vol. 160, No. 1411; 1998; pp. 1411-1418.

Stein et al.; "Interleukin 4 Potently Enhances Murine Macrophage Mannose Receptor Activity: A Marker of Alternative Immunologic Macrophage Activation"; J. Exp. Med.; vol. 176, No. 287; Jul. 1992; pp. 287-292.

Fagnoni et al.; "Role of B70/B7-2 in DC4+ T-Cell Immune Responses Induced by Dendrit c Cells"; Immunology; vol. 85; 1995; pp, 467-474.

Rudd; "Upstream-Downstream: CD28 Cosignaling Pathway and T Cell Function" Immunity; vol. 4; Jun. 1996; 527-534.

Yokose et al.; Studies of Carcinogenicity of Sodium Chlorite in B6C3F1 mice, Environ. Health Perspect.; vol. 76; p. 205-210, 1987.

Cecil Textbook of Medicine, vol. 1(21st Ed. 2000), pp. 376, 433-436, 476, 477, 584, 585, 722-729, 790-796, 818, 819, 876-880, 919-926, 944-953, 962-969.

Cecil Textbook of Medicine, vol. 2 (21st Ed. 2000), pp. 1236, 1237, 1263-1272, 1454-1457, 1492-1507, 1509-1524, 1624-1630, 1757-1761, 2052, 2053, 2221-2223.

McGrath et al., "Effect of WF10 (TCDO) on antigen presentation", Transplantation Proceedings (1998), vol. 30, pp. 4200-4204.

Gillissen et al., "Increased Resistance towards Two Systemic Experimental Infections by Tetrachlorodecaoxygen Anion Complex," Arzneim.-Forsch./Drug Res. vol. 36(III), No. 12, pp. 1778-1782, 1986.

Schubert et al., "The Influence of Aciclovir, Imipenem and Tetrachlorodecaoxide on Murine and Human Lymphocyte Transformation," Zbl. Bakteriol. 1 Abt Orig A (268, No. 4, p. 551 (1988)), Abstract.

Bartkowski et al., "Effects of tetrachlorodecaxodie in a metastasizing lymphosarcoma of the Syrian Golden Hamster", J. Cancer Res. Clin. Oncol, vol. 114, Supp, S162, 1988.

Kempf et al., "Comparative Study on the Effects of Chlorite Oxygen Reaction Product TCDO (Tetrachlorodecaoxygen) and Sodium Chlorite Solution ($NaClO_2$) with Equimolar Chlorite Content on Bone Marrow and Peripheral Blood of BDIX Rats," Drugs Under Experimental and Clinical Research (1993), vol. 19, No. 4, pp. 165-174).

Esltner E.F., "Induction of Oxidative Processes by Tetrachlorodecaoxide," Klin. Wochenschr., Dec. 15, 1991:69:p. 949-956.

Busch et al., Treatment of HIV-Infected Patients with Advanced Symptomatic Disease with WF10 Solution (TCDO), In. Conf. Aids., Aug. 7-12, 1994; (10)(1) p. 204, Abst. #PB0245.

Cotran et al., "Malignant Lymphomas," Chapter 14, Robbins Pathologic Basis of Disease ($5^{th}$ Ed. 1994), p. 634, 635, 643-645, 647.

Rimpler et al., "Balneozoon and hydroxan. Application of halogen-containing oxocomplexes for balneology and the swimming pool area," Forum Staedte-hygine, Patzer Verlag, DE, vol. 43, No. 5, Sep. 1, 1992, pp. 226-230.

McGrath et al., "Balanced Macrophage Activation Hypothesis: A Biological Model for Development of Drugs Targeted at Macrophage Functional States," Pathobiology, vol. 67, pp. 277-281, 1999.

McGrath et al., "Development of WF10, a novel macrophage-regulating agent," Curr. Opin. Investig. Drugs, vol. 3, No. 3, pp. 365-373, Mar. 2002.

Office Action issued on Apr. 30, 2012 by the Examiner in U.S. Appl. No. 12/602,589 (US 2010/0233118).

Notice of Allowance issued on Jul. 16, 2012 by the Examiner in U.S. Appl. No. 12/602,589 (US 2010/0233118).

European Office Action issued in application No. EP 08758884 on Sep. 20, 2011.

\* cited by examiner

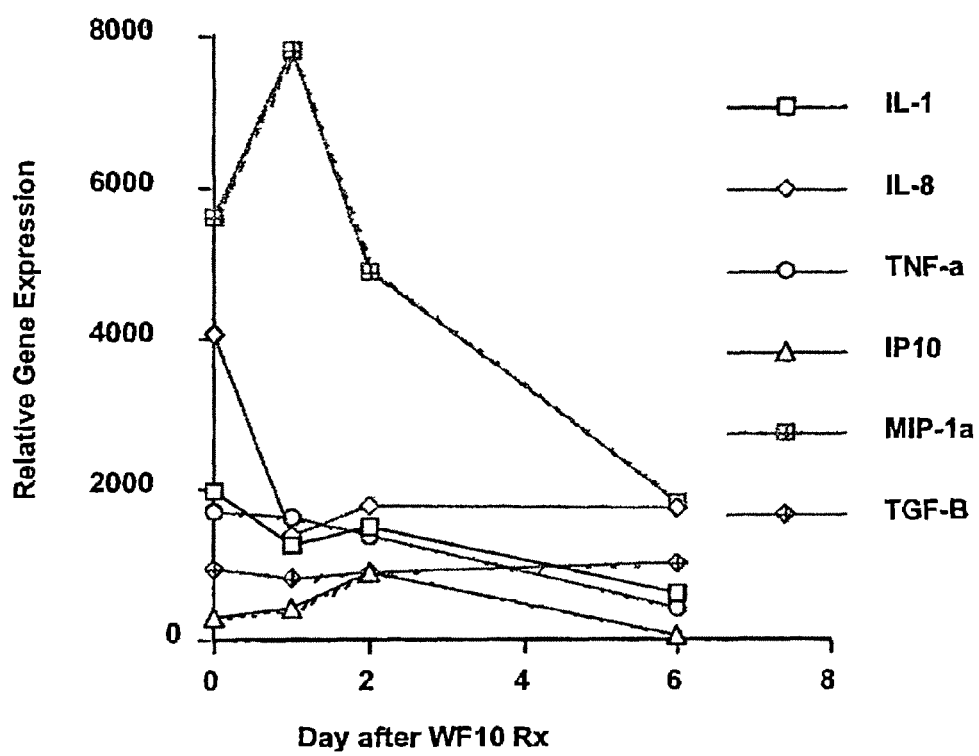

USE OF WF10 FOR TREATING ALLERGIC ASTHMA, ALLERGIC RHINITIS AND ATOPIC DERMATITIS

FIELD OF THE INVENTION

The present invention relates to a method of treating allergic asthma, allergic rhinitis and atopic dermatitis, more particularly the present invention relates to the use of WF10 for such treatment.

BACKGROUND OF THE INVENTION

Allergic rhinitis and allergic asthma are two closely related diseases characterized by an inappropriate reaction of the respiratory system to stimuli. (A. Gillission, G. Hoeffken, U. R. Juergens: *A Connection Between Allergic Rhinitis and Allergic Asthma? The "One-Airway-One-Disease"-Hypothesis. Part 2: Clinical Manifestation, Diagnosis and Shared Therapies*. Pneumologe 59 (2005), 192-200). (J. Bousquet: *Allergic Rhinitis and its Impact on Asthma (ARIA). Clinical & Experimental Allergy Reviews* 3 (1), 43-45). Data from immunologic, genetic and epidemiologic studies point to a systemic link between rhinitis and allergic asthma and which can be seen as manifestations of a common atopic syndrome. Often, the initial reaction of afflicted persons is allergic rhinitis with asthma symptoms appearing years later. These allergic diseases can also progress to affect organs other than the nose, throat and lungs including the eyes, skin and gastrointestinal tract. Additional symptoms include conjunctivitis and other eye related symptoms including eye lid swelling as well as skin related reactions such as atopic dermatitis and psoriasis.

In asthma, the airways become blocked or narrowed causing difficulty breathing. Allergic asthma is characterized by symptoms of coughing, wheezing, shortness of breath or rapid breathing, and chest tightness that are triggered by an allergic reaction to inhaled allergens such as dust mite allergen, pet dander, pollen and mold. Symptoms in asthma patients often can be life threatening. The strong bronchoconstriction and the swelling of the airways can reduce the oxygen and $CO_2$ exchange in the lungs to an extent where patients die from suffocation.

Asthma in general is one of the most common chronic diseases worldwide and a serious global health problem in terms of health care costs and reduced quality of life. People of all ages in countries throughout the world are affected by this disorder although children are particularly susceptible. According to the worldwide Global Initiative for Asthma (GINA), as many as 300 million people worldwide suffer from asthma and this is expected to increase by another 100 million by 2025. Allergic asthma is the most common form, affecting over 50% of sufferers.

Rhinitis symptoms include nasal itching, sneezing, nasal congestion, rhinorrhea (runny nose), and postnasal drainage. Patients with rhinitis frequently have coexisting non-nasal symptoms as well including ocular symptoms, such as itching, swelling, increased lacrimation, and redness. In addition, patients may complain of itching of the throat, constant clearing of secretions from the throat, irritation of the throat, and/or cough. Otic symptoms can include decreased hearing, popping, and fullness. When nasal symptoms are severe, they may be accompanied by itching in the ears and/or palate. There may be interference with aeration and drainage of the paranasal sinuses, resulting in headache or facial pressure or pain. In addition, systemic symptoms, including weakness, malaise, fatigue, poor appetite, and cognitive impairment, have been associated with rhinitis. Allergic rhinitis is not life-threatening, as is allergic asthma, but it can have a significant impact on quality of life.

Generally the treatment of asthmatic patients focuses on measurements of asthma symptoms, sleep disturbance, use of rescue medication, limitations of daily activity, lung function as well as patient and physician assessments. The goal of asthma treatment is well-controlled asthma which is generally regarded as including: symptoms occurring twice per week or less, use of a rescue bronchodilator twice a week or less, no nighttime or early morning awakening, no limitations on exercise work or school, normal peak expiratory flow (PEF) or forced expiratory volume (FEV), Complete or total control of asthma symptoms includes: no asthma symptoms and no rescue bronchodilator use as well as no nighttime or early morning awakening and no limitations on exercise, work or school. Well-controlled asthma is generally a realistic target for most but not all patients. Some patients may wish to achieve complete control. However, some may only be able to achieve well-controlled or completely controlled asthma with medications or doses of medications that cause significant adverse effects. There are also certain patients that can only achieve partial control, for example those with steroid-resistant asthma. In treating allergic asthma, the prevention and interference with life threatening bronchioconstriction episodes is a prime goal (W. T. Watson, A. B. Becker, F. E. Simpson: *Treatment of allergic rhinitis with intranasal corticosteroids in patients with mild asthma: effect on lower airway responsiveness. J Allergy Clin Immunol.* 91 (1993), 97-101).

Several treatment options exist for rhinitis and asthma. However, all treatments known to date provide only symptom modification or even only acute symptom reduction without interfering with the cause of the disease or the disease progression. In general, treatments may be life style modification to reduce the exposure to stimuli, anti-inflammatory medication to relieve the inflammation related symptoms, inflammatory mediator release inhibitors to reduce the effect of single mediators such as histamine or individual interleukins, symptomatic relievers such as anticongestants or bronchodilating agents and finally immune globulins to reduce the immune globulin E driven reaction. With the exception of immune globulin E treatment, the options for achieving control of asthma symptoms require the repeated (daily) prophylactic or metaphylactic administration of drugs. The immune globulin E treatment is the one exception in that it may be administered every few months. There are no treatment options that control the appearance of asthma symptoms for a period of 1 or 2 years.

The complicated combination of chronic medications to reduce the frequency and severity of attacks with short acting inhaled drugs to reduce symptoms during an attack makes clear that current treatments are not optimal. Undesirable drun related side effects arise from the use of steroids and beta agonists. The treatment to reduce immune globulin E antibodies is a useful improvement but the intervention must be repeated every few months. As well with the use of antibodies in general, the likelihood is high that the body will identify the administered antibodies as foreign and develops neutralizing antibodies in response. Furthermore, the current treatments focus on the treatment of symptoms but not of the disease or the cause of the disease. Currently there are no treatments available that prevent the allergic reaction from occurring in response to allergen exposure.

There is thus a medical need to have improved treatments for rhinitis, asthma and atopic diseases such as atopic dermatitis. A therapy that reduces the requirement for daily treatments would be a substantial improvement.

SUMMARY OF THE INVENTION

In one aspect the present invention provides a method of treating allergic asthma, allergic rhinitis and atopic dermatitis using WF10. Further the present invention provides the use of WF10 for such treatment.

In an alternative aspect the present invention provides a method respective the use of WF10 for the reduction, prevention or treatment of allergy like symptoms comprising administering to a patient suffering from allergy like symptoms a therapeutically effective amount of WF10.

BRIEF DESCRIPTION OF THE DRAWINGS

The present invention will be described in further detail below with reference to the accompanying drawing in which:

FIG. 1 is a graph showing blood analysis of gene expression in patient number one relative to days post WF10 treatment.

DETAILED DESCRIPTION OF THE INVENTION

WF10 is a sterile, pyrogen-free, 10% (w/v) aqueous dilute solution of the drug substance OXO-K993, which is analytically characterized as a solution containing the ions chlorite (425%), chloride (2.0%), chlorate (1.5%), sulfate (0.7%), and sodium (4.0%). Human clinical studies have generated substantial evidence of safety when WF10 is infused in a dose of 0.5 mL/kg per day for 5 consecutive days followed by a 16-day drug-free interval, constituting a "cycle". In two protocols, patients received 6 cycles of therapy and in another trial, patients received 4 cycles followed by maintenance use every 6 weeks for up to 128 weeks. In every case, WF10 showed an excellent safety profile with no steroid like side effects, no immune suppression, no antihistamine like side effects and no cardiovascular side effects.

WF10 has been shown to have an impact on macrophage function (M. S. McGrath, C. Benike, F. W. Kuehne, E. Englemann: *Effect of WF10 (TCDO) on antigen presentation. Transplant Proc.* 30 (1998), 4200-4202) by stimulating phagocytosis and reducing the inflammatory phenotype (M. S. McGrath, V. Kodelja: *Balanced Macrophage Activation Hypothesis: A Biological Model for Development of Drugs Targeted at Macrophage Functional States. Pathobiology* 67 (1999), 277-281). The evidence suggests that WF10 might down regulate immunologic activation through removal of the influence of inflammatory macrophages on chronic T cell activation.

However, no steroid like immune-suppressive effect and no anti-histamine like effect have been observed in studies on WF10. Rather an immune system normalization effect has been observed in vitro studies (M. S. McGrath, J. O. Kahn, B. G. Hemdier. *Development of WF10, a novel macrophage-regulating agent. Curr. Opin. Investig. Drugs* 3 (2002), 365-373).

Macrophage function has not been reported to play any key role in symptom expression of allergic rhinitis, asthma or any other atopic disease.

The present invention provides a method of respective the use of WF10 for inhibiting at least one of allergic asthma, allergic rhinitis and atopic dermatitis comprising administering to a subject suffering from at least one of allergic asthma, allergic rhinitis and atopic dermatitis a therapeutically effective amount of WF10.

The present invention also provides a method for the reduction, prevention or treatment of allergy like symptoms comprising administering to a subject suffering from allergy like symptoms a therapeutically effective amount of WF10. Examples of allergy like symptoms that may be reduced, prevented or treated include, but are not limited to, allergic rhinitis symptoms, asthma like symptoms, atopic skin reactions, allergic skin reactions and gastrointestinal allergen related symptoms.

Examples of the types of symptoms described above may include, but are not limited to, the following: symptoms that are associated with allergic rhinitis are described in the background section above and may include nasal itching, sneezing, nasal congestion, rhinorrhea (runny nose), and postnasal drainage; symptoms associated with asthma may include breathlessness, wheezing on exhale, dry cough and a feeling of tightness in the chest; symptoms associated with atopic skin reactions and allergic skin reactions may include scaly skin, itchy skin, inflamed/swollen skin and cracked skin; and symptoms associated with gastrointestinal allergens may include general discomfort, gas and bloating.

It will be understood from the description, and the examples provided, that WF10 may be administered in symptom free patients to prevent the re-occurrence of symptoms, in patients with mild symptoms, or even in patients with moderate to severe symptoms.

Patients may be drug free or drug naïve, or may be receiving any other anti-allergic medication in addition to WF10. As shown in the examples below, administration of WF10 results in a reduction of symptom expression and in a reduction of the need for classical anti-allergic or anti-asthma medication.

WF10 is preferably administered to the subject intravenously. Especially for the inventive use WF10 may thus be co-administered or combined with all currently known anti-allergic medication, given orally, parenterally, topically, via transdermal therapeutic systems, rectally or by inhalation. These medications, as mentioned above, include steroids (inhaled, intranasal, as eye drops, orally or via parenteral, rectal or other routes), antihistamines, beta-agonists, anti-muscarine drugs, immune modulators such as PDE4 inhibitors, leukotrien antagonists, anti-IgE antibodies, and other (innovative) medications. WF10 may also be administered as monotherapy.

One embodiment of the invention is the administration of one treatment cycle of WF10 semi-annually, annually or bi-annually. In one embodiment, a dose of 0.5 ml/kg body weight is administered daily over 5 days as a treatment cycle of infusions. In one example, WF10 is diluted for use with normal saline or dextrose in water and is ideally used within 4 hours of preparation. Refrigerator or freezer storage is not recommended to extend the 4-hour limit. For example, WF10 can be administered as a dose of 0.5 mL/kg of body weight, diluted into at least 250 mL of normal saline and infused over 60-90 minutes. For ease of administration, a standard dose of 50 to 75 mL of WF10 may be administered to adults, regardless of the body weight. Depending on the individual medical need, the dose may be reduced to 0.375, or even 0.1 ml/kg, or as 5 to 50 mg per individual. In young children or sensitive persons on one hand, and in very severely affected or resistant patients on the other hand, the dose may be further adjusted within the range of 0.01 to 2 ml/kg. The dose adjustment is to be performed according to the individual medical need and in line with the decision of the physician prescribing the treatment.

In a further embodiment, the WF10 has a concentration of about 40 to about 80 mMol of $ClO_2$ per liter. In another embodiment, the WF10 has a concentration of about 60 mMol $ClO_2$ per liter.

In one embodiment, an infusion pump may be used for the administration of WF10. In one embodiment, infusions are administered daily on consecutive days (for example each day for 5 consecutive days), but it is also possible to administer the drug every other day or to prolong the breaks between infusions to 2 or 3 days, accommodating weekends and holidays without interference with the pharmacological effect. In one embodiment, one cycle constitutes 5 infusions. However, since good effects have been seen after 2 to 3 infusions, the treatment may also consist of a short cycle of 2 or 3 or 4 infusions. In individual cases, a single infusion may be sufficient.

In one embodiment, the administration of WF10 to a subject may consist of 1 to 6 daily infusions within a 7 to 28 day period, or alternatively within a 7 to 21 day period or within a 7 to 14 day period. In another embodiment the administration of WF10 to a subject may consist of 2 to 5 daily infusions within a 7 to 28 day period, or within a 7 to 21 day period or within a 7 to 14 day period. Alternatively, the administration of WF10 to a subject may consist of 3 to 5 daily infusions within a 7 to 28 day period, or alternatively within a 7 to 21 day period or within a 7 to 14 day period. Alternatively, the administration of WF10 to a subject may consist of 4 to 5 daily infusions within a 7 to 28 day period, or within a 7 to 21 day period or within a 7 to 14 day period.

In another embodiment, the administration of WF10 to a subject may consist of 1 to 6 daily infusions within a 7 day period. Alternatively, within the 7 day period, the WF10 may be administered to the subject as 2 to 5 daily infusions or alternatively as 3 to 5 daily infusions or 4 to 5 daily infusions.

While the cycles may be repeated as frequently as every 2 to 3 weeks, the treatment interval may be semi-annually, annually or bi-annually. The treatment interval for each cycle may be adjusted to meet the individual symptoms. A single course will be sufficient to reduce the symptoms for a prolonged period, but in severely affected individuals, two or three cycles spaced every 2 to 4 weeks may be necessary to suppress or largely reduce the symptoms. As soon as a good therapeutic effect is reached, no further cycles are needed until re-occurrence of the symptoms which may be for one or two years. Alternatively, to prevent the re-occurrence, the treatment may be repeated every year or every two years, for example, or in heavily affected individuals twice a year, or more frequently if desired.

A treatment cycle within the above mentioned dose range may also be made in combination with a treatment cycle of anti-IgE (for example Omalizumab) or anti-TNFalpha antibodies or other anti-inflammatory drugs to reduce the inflammatory reaction. This may be especially needed in severely affected individuals which are in need to remain exposed to the allergen, such as farmers with farmer's lung or other employees who can not reduce the allergen exposure, or in other individuals in need of the strongest medication available.

The treatment cycles may be also combined with steroid administration (inhaled, intranasal, topical or oral) and all other anti-allergic or anti-asthma medication. To support the pharmacological effect especially during the first days of a treatment cycle, the infusion therapy may be also combined with bronchodilating agents such as beta-agonists or anti-cholinergics, with anti-congestants in patients with allergic rhinitis, with anti-allergic eye drops, with antihistamines, with topical creams such as topical immune modulators (TIMS) such as pimecrolimus or tacrolimus or cyclosporine (topical or systemically) in patients with atopic dermatitis or psoriasis symptoms and other patients in need thereof, with topical steroids in patients with atopic dermatitis or psoriasis. The infusion cycles may also be combined with educational treatment and counselling to improve the living habits and to learn to cope with acute symptoms of asthma or other allergic diseases and with other adjuvant treatments including but not limited to acupuncture, acupressure, physical therapy, and, especially in the case of atopic dermatitis or psoriasis, cosmetic therapy to improve further the quality of life and to help reach quickly a normal symptom free living or a living at a largely reduced symptom level.

The present invention further provides a method of reducing the expression of at least one proinflammatory agent, for example, a cytokine and/or a chemokine, in a subject suffering from allergy like symptoms. Pro-inflammatory agents are agents that are known to play an active role in the inflammatory process, such agents are documented and known in the art. In one embodiment a method is provided for reducing the expression of at least one pro-inflammatory agent, for example MIP-1a, IL-8, IL-1, and TNF-alpha, and in particular MIP-1a and IL-8, in a subject suffering from allergy like symptoms, comprising administering WF10 to the subject. The administration of the WF10, for the reduction in the expression of at least one pro-inflammatory agent, occurs as described herein. For example, the administration of the WF10 may consist of 4 daily infusions during a 6 or 7 day period.

It will be understood that the present invention is directed towards the treatment of a subject that includes mammals, for example humans, horses, cats and dogs.

In one embodiment the present invention provides for the use of WF10 for the prevention, metaphylaxis or treatment of allergy like symptoms In a further embodiment the present invention provides for the use of WF10 for the prevention, metaphylaxis or treatment of allergy like symptoms including but not limited to allergic rhinitis like symptoms, asthma like symptoms, atopic or allergic skin reactions, or gastrointestinal allergen related reactions in subject.

Such reactions are well known for horses where allergic rhinitis and asthma like symptoms are very frequent and have a huge impact on quality of life of the horse and on usability for the owner. Allergens responsible for the reactions often are found in hay, but also in bedding and food. However, cats and dogs are also known to express allergic rhinitis or asthma like symptoms. In dogs, the organ which reacts most frequently to allergens (in contrast to human beings) is the skin. Dogs and often also cats develop severe atopic dermatitis or allergic dermatitis and in both species, and other species, the second organ which often manifests allergic reactions is the gastrointestinal system. Indeed, allergic diarrhoea is frequent in dogs.

WF10 may be infused at a dose of 0.5 ml/kg with up to 5 infusions administered in one course and with repetition of the treatment cycles every few weeks or more likely once a year or even less frequent, depending on the symptoms of the animal. As with human beings, the dose and frequency of administration may be adjusted according to the individual need of the animal.

According to the present invention, and as described below, WF10 was administered to 4 patients with allergic rhinitis, allergic rhinitis with asthma or allergic rhinitis with asthma and atopic or allergic dermatitis. All four patients had previously reported a broad spectrum of allergic reaction. Two patients had used their daily anti-allergic medication for years. In every case, the patients had been suffering from their individual diseases for many years and had used numerous different drugs, with varying effect but never with full satisfaction.

In patients, suffering from their symptoms for many years, a significant clinical benefit of WF10 treatment was observed. Unexpectedly, the symptom reduction persisted for a very long period of time after cessation of the therapy. A similar long lasting effect on the allergic reaction, to a point where no active drug can be found in the body, has not been reported for any known anti-allergic drug.

The following examples serve to illustrate preferred embodiments of the present invention. Those skilled in the art will recognise that various modifications may be made to the foregoing description and the following examples and that the following examples are not meant to be limiting with respect to the scope of the invention.

EXAMPLE 1

Case Report of Patient #1

A male patient (date of birth Sep. 21, 1963) presented with allergic rhinitis and allergic bronchial asthma. Over a 25 year period, the patient exhibited a wideband allergic reaction each year from early February until late October with asthmatic component. During that 25 year period, additional clinical manifestations of neurodermatitis occurred, especially head, face and fingers with open encrusted skin areas, painful and extreme dry skin areas, blistering skin.

Subsequent to the 25 year period mentioned above, and during a period of extreme allergic rhinitis with bronchial asthma, 4 daily infusions of WF10 within one week were administered. After 10 days, the patient was symptom free for two years after which the symptoms returned but were less severe.

Several medications were used prior to the first experience with WF10. During 25 years different allergen-desensitizing therapies: oral therapy, injection cycles over 2 to 3 years combined with permanent oral medication. Results were permanent tiredness without significant therapy effects. Exception was with Kenalog (Triamcinolone intramuscular), however, side effects were not acceptable.

Medications that were used included: Tavegyl (clamestin, antihistamine), Dehistin (histamine h1 antagonists), Kenalog (Triamcinolone intramuscular), and Intal (cromolyn sodium inhalation aerosol).

Stop of all therapy options to treat allergic rhinitis and bronchial asthma by the patient during the above mentioned 25 year period. In that period, topical application of corticoids was administered because of neurodermatitis. Within this period there were 2 episodes of prednisolon application because of acute status of neurodermatitis.

During a 5 year period in the above mentioned 25 year period, no other antihistamine or antiallergic medication were administered. The only exception was an emergency aerosol to treat acute broncial asthma.

The patient was treated with WF10 using a dose of 0.5 ml/kg body weight. WF10 was administered to the patient on day 1. day 2, day 3, day 6. There were no measurable effects reported by patient during treatment period.

About 10 days after start of infusions, the patient was abruptly free of any symptoms of allergic rhinitis and asthma. This continued through for 2 years following therapy after which the therapy was repeated biannually with the same doctor and the results were reproduced each time.

In addition, the patient changed their physical location to a place which had a distinct difference in vegetation and spectrum of allergens from the previous location. Symptoms of allergic rhinitis and bronchial asthma were still improved despite this change. One day was needed for acclimatization to the new environment and thereafter the patient was symptom free.

Blood analysis of gene expression in patient #1 relative to days post WF10 treatment is graphically depicted in FIG. 1. Blood samples were taken before each treatment and analysed using light cycler technology. Values taken at Day 0 were pre-WF10 treatment. Samples taken on day 1 were taken after the first infusion, samples taken on day 2 after the second infusion and samples taken on day 6 after the fourth infusion. As can be seen from FIG. 1 there is a significant reduction in the expression of IL-8 and MIP-1a after WF10 treatment. An overall reduction is also seen for IL-1, TNF-α and IP10.

EXAMPLE 2

Case Report of Patient #2

A female patient (date of birth Mar. 1, 1955) presented with allergic rhinitis and allergic bronchial asthma. There was an initial diagnosis of allergic rhinitis and bronchial asthma in 1996. Before 1996, the symptoms were diagnosed and treated as colds several times per year. Symptoms between the end of January/February and October were characterised as hay fever with bouts of sneezing (up to 20 times per bout), sore throats, headache, inflamed eyes and ears, allergic asthma, and neurodermatitis.

The otorhinolaryngologist did not recommend an allergen-desensitizing therapy because of the wideband allergic spectrum.

Medications used prior to the administration of WF10 included years of daily application within period of allergen exposure of several prescription medications. The last ones to be used were: Telfast (Fexofenadin), Cromo-CT eye drops (Natriumcromoglicat), Vividrin acute nose spray (Azelastin), Symbicord-Turbohaler and Dermatop salve (Cortison)

Antiallergic medications used within the last 3 weeks before first WF10 application included: Telfast, eye drops, nose spray, Symbicord and Dermatop.

The patient was administered WF10 at a dose of 0.5 ml/kg body weight. The application days were: 6 (½ dose)/7/8/15/16/20 (½ dose) Jun., 2006.

The course of treatment and overall assessment after infusion on application day was as follows. On a scale ranging from 1 to 6, 1 being the best and 6 the worst possible disease rating, the patient reported the following disease seventies: day 7—General status rated 3 with additional medication as before; day 8—General status rated 2 without additional medication; day 15—Significant improvement, just slight medical conditions regarding throat and respiratory system, only minor symptoms of rhinitis observed; day 16—Minor symptoms of rhinitis decreasing, no headache, no coughing even after high exposure to grass pollen; and day 20—Overall status rated 2, slight skin irritation at palms. Total constitution excellent, especially in the morning without any problems with inflamed eyes.

Overall improvement of the patient's general condition. Physical capacity significantly improved. Drastic improvement recognizable after third infusion. No other medications necessary with exception of Dermatop salve for topical application to skin areas with neurodermatitis. Patient continued through summer allergy season without any other medication, symptom free for the rest of 2006 and 2007. Symptoms returned in 2008 and the patient was subsequently treated with WF10.

Only side effect after initial WF10 treatment was slight skin irritation at palms 10 days after infusion. Patient very satisfied with treatment.

EXAMPLE 3

Case Report of Patient #3

A female patient (date of birth Oct. 25, 1954) presented with allergic rhinitis and allergic bronchial asthma. Diagnosis of allergic rhinitis and bronchial asthma occurred in 1990. Symptoms of allergic rhinitis and bronchial asthma characterized by sneezing bouts, headache, inflamed eyes, cough, respiratory depression as well as neurodermatitis. Symptoms present between the end of January/February and October/November.

Several medications were used prior to the administration of WF10. Over years, daily application within period of allergen exposition of several medications available only on prescription. The last ones included: Xusal (Levocetirizin), Cromo-CT eye drops (Natriumcromoglicat), Vividrin acute nose spray (Azelastin), and Symbicord-Turbohaler.

Antiallergic medications were used within the last 3 weeks before first WF10 application and included: Xusal, eye drops, nose spray, Symbicord (several times a day as necessary)

The patient was administered WF10 at a dose of 0.5 ml/kg body weight. The application days were: 5/8/11/18/19 Sep., 2006.

The course of treatment and overall assessment after infusion on application day was as follows. Application of any antiallergic drug (see above) stopped before first WF10 infusion: day 8—nose itching, inflamed eyes; day 11 (without additional medication)—nose itching, inflamed eyes; day 18 (without additional medication)—nose itching decreased, eyes symptom free; and day 19 (without additional medication)—symptoms further decreased. Significant overall improvement in patient's general condition recognizable after third infusion.

Patient was symptom free in 2006 and was very satisfied with treatment. The patient reported a recurrence of hay fever symptoms in 2007 but these symptoms were milder than those reported before the WF10 treatment. No hay fever symptoms reported in first quarter of 2008.

Main allergy season is between March and June. Prior to WF10 therapy the patient could not go through the allergy season without antiallergic medications.

EXAMPLE 4

Case Report of Patient #4

Patient experienced annual allergy symptoms for the past 25 years. The symptoms included excessively swollen eyes, especially in the morning; strong itching in the eyes; continuously running nose; headache; and sense of fatigue (without medication). The symptoms typically started in mid-February at the start of hey fever season and culminated in April and May during the movement of birch pollen. The symptoms usually subsided thereafter.

The patient has a known allergy to birch pollen and early prospering plants like hazelnut and willow trees, and a known a cross-reaction with certain kinds of apples (experiencing a transient furry feeling in the mouth).

Medications until first experience with WF10:

The patient has tried a variety of medications including, eye drops, nasal sprays like cortisone, antihistamines, and homeopathic (e.g. HT 17) and naturopathic treatments. However, nothing has really helped, except the nasal cortisone spray.

The patient received 5 daily infusions of WF10 from February 12 to 16.

At the start of treatment the patient had no impression of improvement, but as the allergy season progressed, the patient reported that the allergy symptoms were not as pronounced as in previous years. The patient reported a substantial improvement of quality of life during birch pollen movement. The allergy symptoms did not disappear totally, but were considerably less obtrusive (eyes as well as nose). Further, the patient reported that symptoms such as fatigue and headache were virtually not existent.

In summary, the patients experienced the following improvement: One patient had stopped his standard daily medication before first infusion of WF10 and after the infusions there was no need for any additional medication. A second patient reduced standard medication during WF10 therapy. Two patients reported overall improvement of symptoms after second and third infusion, respectively. About two weeks after first infusion patients were free of symptoms without any medication including administration of topical steroids.

The patient with more than 30 years of disease history and atopic dermatitis had been treated the first time under highest expression of symptoms of allergic rhinitis as well as allergic asthma. One cycle of WF10 resulted in a symptom free status after about 10 days, followed by a symptom free season in 2 subsequent years. Thereafter, symptoms became present again in early spring, and the therapy had been repeated with same clinical observation and success. Meanwhile this regimen has been applied 5 times to that patient every two years and every time with good success.

It can be concluded from the above that one cycle of WF10 every one to two years can give patients suffering from different allergic reactions including rhinitis, conjunctivitis, asthma, atopic dermatitis and psoriasis, one to two symptom free years. The side effect profile is excellent and side effects if observed at all are related to the infusion technology but likely not to the drug effect. No chronic side effects have been observed.

While this invention has been described with reference to illustrative embodiments and examples, the description is not intended to be construed in a limiting sense. Thus, various modification of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

Any publications, patents and patent applications referred to herein are incorporated by reference in their entirety to the same extent as if each individual publication, patent or patent application was specifically and individually indicated to be incorporated by reference in its entirety. Even it is not expressively stated with respect to the described embodiment, also the use of WF10 for the described treatment with some or all of the further features described in connection with the treatment is subject of the present invention.

Further, the described use of WF10 should also comprise the use of WF10 in the manufacture or preparation of a medicament for the treatment described in the present application.

What is claimed is:

1. A method of treating or inhibiting at least one of allergic asthma, allergic rhinitis and atopic dermatitis or reducing, inhibiting or treating allergy-like symptoms in a subject suffering from allergy-like symptoms, wherein the allergy-like symptoms are selected from the group consisting of:

allergic rhinitis symptoms selected from the group consisting of nasal itching, sneezing, nasal congestion, rhinorrhea, postnasal drainage, throat itching, constant clearing of secretions from the throat, throat irritations, cough, ear itching, palate itching, headache, facial pressure, facial pain, ocular symptoms selected from the group consisting of itching, swelling, increased lacrimation and redness, otic symptoms selected from the group consisting of decreased hearing, popping and fullness, and systemic symptoms selected from the group consisting of weakness, malaise, fatigue, poor appetite and cognitive impairment;

asthma-like symptoms selected from coughing, wheezing, shortness of breath, and chest tightness;

atopic skin reactions and allergic skin reactions selected from scaly skin, itchy skin, inflamed skin, swollen skin and cracked skin; and gastrointestinal allergen related symptoms selected from general discomfort, gas and bloating, the method comprising administering to the subject a therapeutically effective amount of a pharmaceutical composition comprising chlorite, chloride, chlorate and/or sulfate ions, wherein the treatment is effected not more than once every 6 months, once every year, or once every two years.

2. The method of claim 1, wherein the pharmaceutical composition comprises chlorite ($ClO_2^{-1}$).

3. The method of claim 2, wherein the pharmaceutical composition comprises about 40 to about 80 mMol $ClO_2^-$ per liter.

4. The method of claim 2, wherein the pharmaceutical composition comprises about 60 mMol $ClO_2^{-1}$ per liter.

5. The method of claim 2, wherein the pharmaceutical composition further comprises chlorate.

6. The method of claim 1, wherein the pharmaceutical composition comprises WF10.

7. The method of claim 1, wherein the pharmaceutical composition consists of WF10.

8. The method of claim 1, wherein the pharmaceutical composition is administered in a range from about 0.01 ml/kg to 2 ml/kg body weight of the subject.

9. The method of claim 8, wherein the pharmaceutical composition is administered in a range from about 0.1 ml/kg to about 1.5 ml/kg body weight of the subject.

10. The method of claim 8, wherein the pharmaceutical composition is administered at about 0.5 ml/kg body weight of the subject.

11. The method of claim 1, wherein the pharmaceutical composition is administered as a treatment of 1 to 6 daily administrations within a 7 day period.

12. The method of claim 11, wherein the pharmaceutical composition is administered to the subject in accordance with a treatment selected from the group consisting of (i) 1 to 6 daily infusions within a 7 day period, (ii) 2 to 5 daily infusions within a 7 day period, (iii) 3 to 5 daily infusions within a 7 day period, (iv) 4 to 5 daily infusions within a 7 day period, and (v) daily for 5 consecutive days.

13. The method of claim 1, wherein the treatment is effected not more than once every year or once every two years.

14. The method of claim 1, further comprising administering to the subject at least one agent selected from the group consisting of anti-IgE, anti-TNFalpha antibodies, anti-inflammatory agents, steroids, anti-allergic agents, and anti-asthma agents.

15. The method of claim 1, wherein the subject is a mammal.

16. The method of claim 1, wherein the subject is a human.

17. The method of claim 1, wherein the method comprises reducing, inhibiting or treating allergy-like symptoms.

18. The method of claim 17, wherein the allergy-like symptoms are at least one selected from the group consisting of:

allergic rhinitis symptoms selected from the group consisting of nasal itching, sneezing, nasal congestion, rhinorrhea, postnasal drainage, throat itching, constant clearing of secretions from the throat, throat irritations, cough, ear itching, palate itching, headache, facial pressure, facial pain, ocular symptoms selected from the group consisting of itching, swelling, increased lacrimation and redness, otic symptoms selected from the group consisting of decreased hearing, popping and fullness, and systemic symptoms selected from the group consisting of weakness, malaise, fatigue, poor appetite and cognitive impairment.

19. The method of claim 18, wherein persistence of the allergy like symptoms is reduced for a period of time following administration of the pharmaceutical composition selected from the group consisting of six months, one year, and two years.

20. The method of claim 1, wherein the pharmaceutical composition is administered intravenously.

* * * * *

UNITED STATES PATENT AND TRADEMARK OFFICE
CERTIFICATE OF CORRECTION

PATENT NO. : 8,435,568 B2
APPLICATION NO. : 13/560032
DATED : May 7, 2013
INVENTOR(S) : Mathias Brosz et al.

It is certified that error appears in the above-identified patent and that said Letters Patent is hereby corrected as shown below:

In the Specification

Column 2, line 14, please delete "(FEV)," and insert -- (FEV). --.

Column 2, line 55, please delete "drun" and insert -- drug --.

Column 3, line 12, please delete "allergy like" and insert -- allergy-like --.

Column 3, line 29, please delete "(425%)" and insert -- (4.25%) --.

Column 5, line 2, please delete "$ClO_2$" and insert -- $ClO_2^-$ --.

Column 5, line 4, please delete "$ClO_2$" and insert -- $ClO_2^-$ --.

In the Claims

Column 11, Claim 2, line 37, please delete "$ClO_2^{31}$" and insert -- $ClO_2^-$ --.

Column 11, Claim 4, line 42, please delete "$ClO_2^{31}$" and insert -- $ClO_2^-$ --.

Column 12, Claim 19, line 44, please delete "allergy like" and insert -- allergy-like --.

Signed and Sealed this
Second Day of July, 2013

Teresa Stanek Rea
*Acting Director of the United States Patent and Trademark Office*